United States Patent [19]

Teranishi et al.

[11] Patent Number: 4,657,916
[45] Date of Patent: Apr. 14, 1987

[54] QUINOLINE-N-OXIDE DERIVATIVE AND PHARMACEUTICAL COMPOSITION

[75] Inventors: Masayuki Teranishi; Koji Suzuki, both of Machida; Hiroshi Kase, Koganei; Shigeto Kitamura, Machida; Katsuichi Shuto, Shizuoka; Kenji Omori, Mishima, all of Japan

[73] Assignee: Kyowa Hakko Kogyo Co., Ltd., Tokyo, Japan

[21] Appl. No.: 772,693

[22] Filed: Sep. 5, 1985

[30] Foreign Application Priority Data

Sep. 7, 1984 [JP] Japan ................ 59-187752

[51] Int. Cl.$^4$ ............ A61K 31/47; C07D 215/60
[52] U.S. Cl. ............ 514/312; 546/153; 546/155; 546/156
[58] Field of Search ............ 546/153, 156, 155; 514/312

[56] References Cited

PUBLICATIONS

Nippon Lederle, Chemical Abstracts 101:72630g.

Primary Examiner—Sam Rosen
Assistant Examiner—Robert Benson
Attorney, Agent, or Firm—Antonelli, Terry & Wands

[57] ABSTRACT

A quinoline-N-oxide derivative represented by the formula:

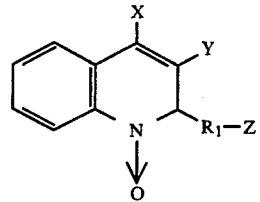

wherein X is hydroxy, lower alkoxy, lower alkylthio, unsubstituted or substituted aralkyloxy, or unsubstituted or substituted aralkylthio; Y is a hydrogen atom or halogen atom; $R_1$ is alkylene or alkenylene having 3 to 15 carbon atom; Z is hydroxymethyl, lower alkoxymethyl, unsubstituted or substituted aryloxymethyl, tetrahydropyranyloxymethyl, tetrahydrofuranyloxymethyl, unsubstituted or substituted arylsulfonyloxymethyl, lower alkylthiomethyl, unsubstituted or substituted arylthiomethyl, lower alkylsulfinylmethyl, unsubstituted or substituted arylsulfinylmethyl, lower alkylsulfonylmethyl, unsubstituted or substituted arylsulfonylmethyl, aminomethyl, —$CH_2NHR_2$ (wherein $R_2$ is lower alkyl, unsubstituted or substituted aralkyl, or unsubstituted or substituted aryl), —$CH_2NR_3R_4$ (wherein $R_3$ and $R_4$ are lower alkyl, unsubstituted or substituted aralkyl, or unsubstituted or substituted aryl), —$CH_2N^+R_5R_6R_7$ (wherein $R_5$, $R_6$, and $R_7$ are lower alkyl, unsubstituted or substituted aralkyl, or unsubstituted or substituted aryl, where the counterion is an anion of acid or a hydroxyl ion), —$COR_8$ (wherein $R_8$ is a hydrogen atom, lower alkyl or hydroxy), —CH-(OR$_9$)$_2$ (wherein $R_9$ is lower alkyl), iminomethyl, hydroxyiminomethyl, or a halogen atom and its salts, can very strongly inhibit the lipoxygenase and considerably suppress production and release of its metabolites, and thus are useful as preventive and healing agents for the diseases caused by the lipoxygenase metabolites.

4 Claims, No Drawings

QUINOLINE-N-OXIDE DERIVATIVE AND PHARMACEUTICAL COMPOSITION

BACKGROUND OF THE INVENTION

The present invention relates to a quinoline-N-oxide derivative having a lipoxygenase-inhibiting action and a pharmaceutical composition containing the same.

Lipoxygenase (1. 13. 11. 12) is an enzyme existing in blood platelets, leukocytes, lymphocytes, etc., and converts polyvalent unsaturated fatty acid (particularly arachidonic acid) to hydroperoxy acid. It is known that positions of hydroperoxy group(s) introduced in arachidonic acid by lipoxygenase are 5th, 8th, 9th, 11th, 12th and 15th positions. For example, it has been reported that lipoxygenase existing mostly in blood platelets, etc. is an enzyme that hydroperoxidizes the 12th position of arachidonic acid (12-lipoxygenase), and there are 5-lipoxygenase and 15-lipoxygenase in leukocytes. Hydroperoxyeicosatetraenoic acid formed from arachidonic acid by lipoxygenase is unstable and is converted to hydroxyeicosatetraenoic acid. These fatty acids formed by lipoxygenase stimulate by themselves physiological actions such as migration of leukocytes and smooth muscles of aortic tunica media, etc., and it has been recently clarified that they are further metabolized in vivo to produce metabolic products having various physiological actions. For example, chemical structure and biosynthesis route of a slow reacting substance of anaphylaxis (abbreviated as SRS-A, which includes leukotriene C, D, E and F) which is formed in lungs of guinea pigs at anaphylaxis or human lungs at asthmatic attacks and has a force to slowly but strongly contract the smooth muscles of bronchus and which has long been regarded as a substance to cause asthma have been recently clarified by Samuelson et al. [Proc. Natl. Acad. Sci. U.S., 77, 2014 (1980)], and it has been found that it is formed by metabolism from arachidonic acid by aid of 5-lipoxygenase. It has been reported that various peroxy lipids such as hydroperoxyeicosatetraenoic acid, hydroxyeicosatetraenoic acid, leucotriene B, SRS-A, etc. which are formed by metabolism by aid of lipoxygenase, are chemical mediators that contract various smooth muscles, for example, smooth muscles of respiratory system (trachea, bronchus, pulmonary tissue), vascular system, digestive organ, accelerate capillary permeability, stimulate migration of leukocytes and smooth muscles of aortic tunica media, and as the result cause bronchial asthma, allergic diseases (atopic dermatitis, inflammation of organs, etc.), diseases of circulatory organs (edema, ischemic heart disease, hypertension, ischemic brain disturbance, arteriosclerosis, etc.) or cause inflammatory diseases.

However, studies of effective compounds on the diseases caused by the lipoxygenase metabolites have not been advanced yet.

As a result of searching preventive and healing agents for the diseases caused by the lipoxygenase metabolites, it has been found that quinoline-N-oxide derivatives are useful as preventive and healing agents, for the diseases caused by the lipoxygenase metabolites.

SUMMARY OF THE INVENTION

The present invention relates to a quinoline-N-oxide derivative represented by the formula (I):

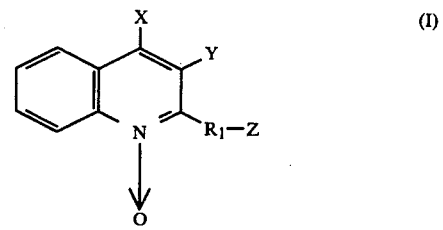

[wherein X is hydroxy, lower alkoxy, lower alkylthio, unsubstituted or substituted aralkyloxy, or unsubstituted or substituted aralkylthio; Y is a hydrogen atom or halogen atom; $R_1$ is alkylene or alkenylene having 3 to 15 carbon atoms; Z is hydroxymethyl, lower alkoxymethyl, unsubstituted or substituted aryloxymethyl, tetrahydropyranyloxymethyl, tetrahydrofuranyloxymethyl, unsubstituted or substituted arylsulfonyloxymethyl, lower alkylthiomethyl, unsubstituted or substituted arylthiomethyl, lower alkylsulfinylmethyl, unsubstituted or substituted arylsulfinylmethyl, lower alkylsulfonylmethyl, unsubstituted or substituted arylsulfonylmethyl, aminomethyl, —CH$_2$NHR$_2$ (wherein $R_2$ is lower alkyl, unsubstituted or substituted aralkyl, or unsubstituted or substituted aryl), —CH$_2$NR$_3$R$_4$ (wherein $R_3$ and $R_4$ are lower alkyl, unsubstituted or substituted aralkyl, or unsubstituted or substituted aryl), —CH$_2$N$^+$R$_5$R$_6$R$_7$ (wherein $R_5$, $R_6$ and $R_7$ are lower alkyl, unsubstituted or substituted aralkyl, or unsubstituted or substituted aryl, where the counterion is an anion of acid or a hydroxyl ion), —COR$_8$ (wherein $R_8$ is a hydrogen atom, lower alkyl or hydroxy), —CH(OR$_9$)$_2$ (wherein $R_9$ is lower alkyl), iminomethyl, hydroxyiminomethyl or a halogen atom] [hereinafter referred to as "compound (I)", and compounds of other formula numbers will be hereinafter likewise referred to] and its salts, and a pharmaceutical composition containing a compound (I) or a pharmacologically acceptable salt thereof. Compounds (I) and their salts can very strongly inhibit the lipoxygenase and considerably suppress production and release of its metabolites, and thus are useful as preventive and healing agents for the diseases caused by the lipoxygenase metabolites.

DETAILED DESCRIPTION OF THE INVENTION

The compound (I) where X=OH can exist as a tautomer as shown by the following equation, and thus it is needless to say that the present invention includes these tautomers:

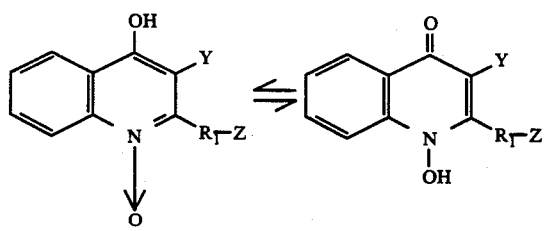

In the definitions of the respective groups in the formula (I), the lower alkyl appearing in the lower alkoxy, lower alkylthio, lower alkylsulfinyl, lower alkylsulfonyl, and lower alkyl includes linear or branched alkyls having 1 to 4 carbon atoms, for example, methyl, ethyl, n-propyl, i-propyl, n-butyl, etc.

In the definitions of the respective groups, the aralkyl appearing in the aralkyloxy, aralkylthio, and aralkyl includes those whose aryl moiety is phenyl or naphthyl and whose alkyl moiety is alkyl having 1 to 3 carbon atoms, for example, methyl, ethyl, etc.

In the definitions of the respective groups, the aryl appearing in the aryloxy, arylthio, arylsulfonyl, and aryl is phenyl or naphthyl. The substituent appearing in the substituted aralkyloxy, substituted aralkylthio, substituted aralkyl, substituted aryloxymethyl, substituted arylsulfonyloxymethyl, substituted arylthiomethyl, substituted arylsulfinylmethyl, substituted arylsulfonylmethyl, and substituted aryl is a substituent on the aryl ring and includes lower alkyl, lower alkoxy, halogen atoms (chlorine, bromine, etc.), nitro, hydroxyl, etc., where the lower alkyl and lower alkoxy have the same meanings as defined above.

In the definitions of the respective groups in the formula (I), the halogen atom includes chlorine, bromine, iodine, etc. The alkylene and alkenylene having 3 to 15 carbon atoms as $R_1$ are linear or branched, and include, for example, trimethylene, pentamethylene, heptamethylene, octamethylene, nonamethylene, decamethylene, undecamethylene, dodecamethylene, tridecamethylene, tetradecamethylene, pentadecamethylene, propenylene, etc. From the viewpoint of pharmacological effect, alkylene and alkenylene having 5 to 15 carbon atoms are preferable.

When the compound (I) is an acidic compound, a base addition salt can be prepared, whereas when it is a basic compound, an acid addition salt can be prepared. The salt of the acidic compound is preferably a pharmacologically acceptable salt, and includes alkali metal salts such as sodium salt and potassium salt, alkaline earth metal salts such as calcium salt and magnesium salt, and salts of organic bases such as ethanolamine, triethylamine, morpholine, piperidine, piperazine, etc. The acid salt of the basic compound includes inorganic and organic acid salts, and such an acid salt is preferably a pharmacologically acceptable salt and includes, for example, hydrochloride, sulfate, nitrate, acetate, oxalate, fumarate, citrate, etc.

The compound (I) can be prepared according to the following reaction procedures:

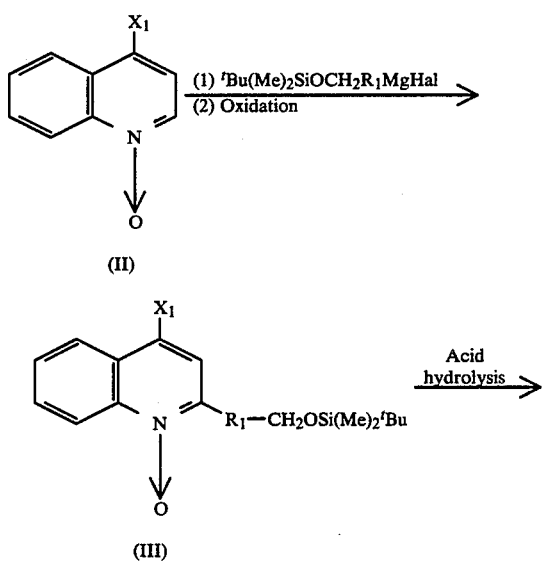

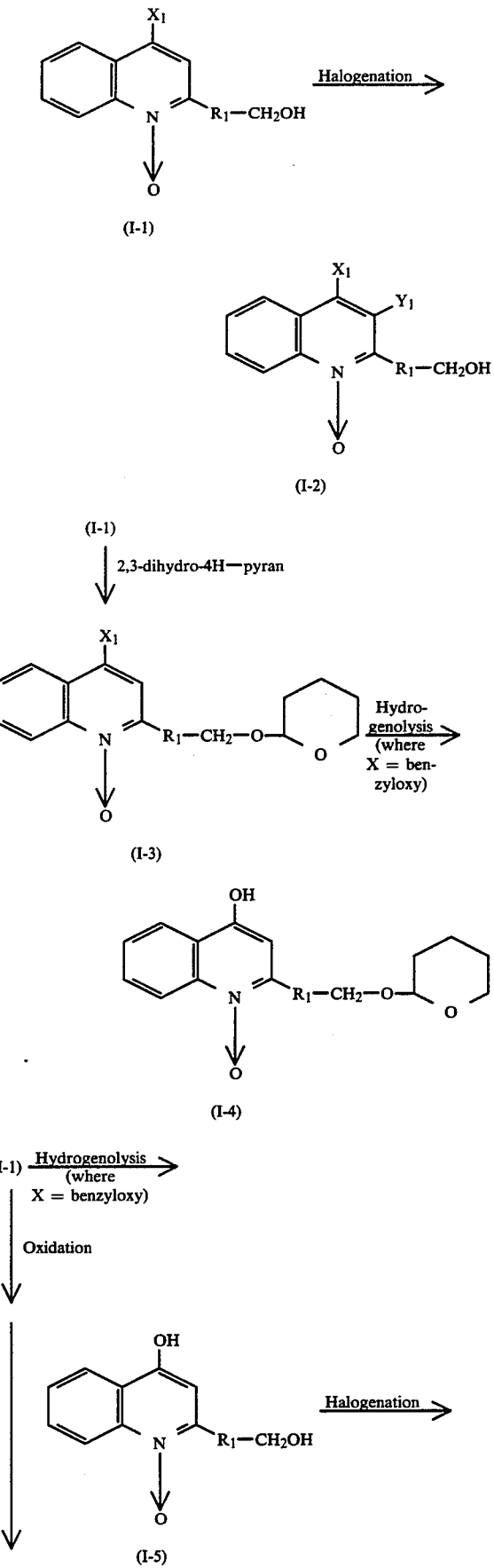

-continued
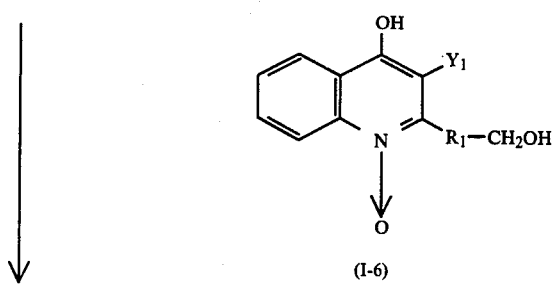
(I-6)
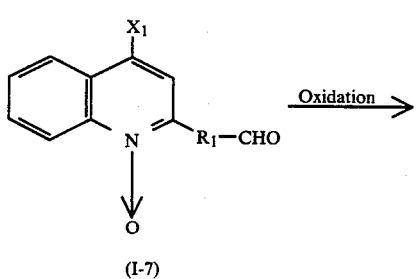
(I-7)
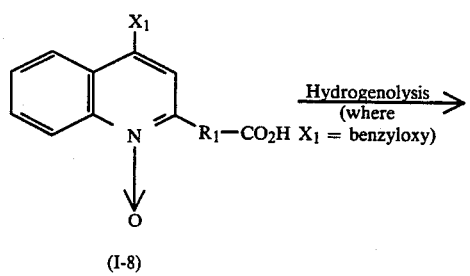
(I-8)
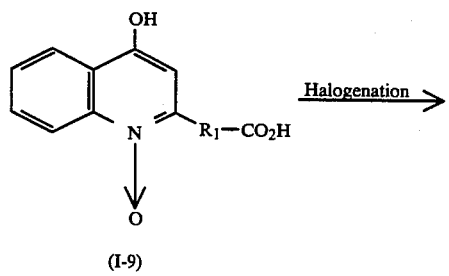
(I-9)
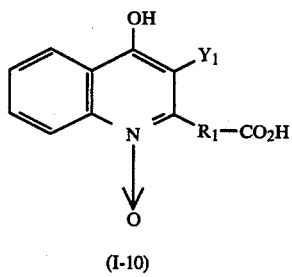
(I-10)
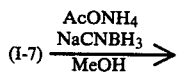
-continued
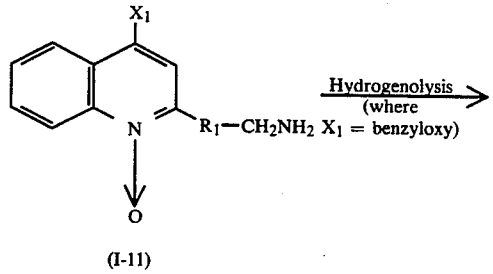
(I-11)
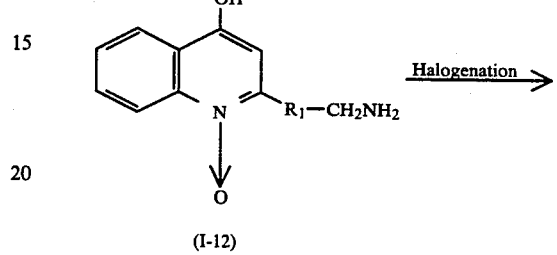
(I-12)
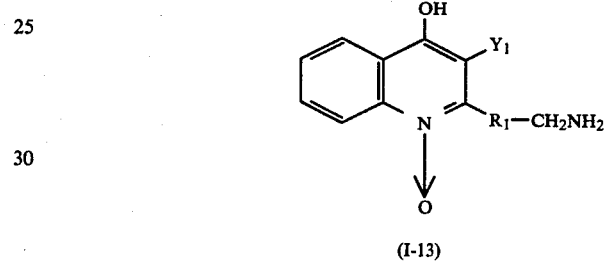
(I-13)
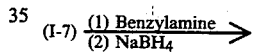
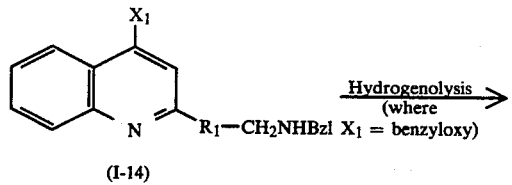
(I-14)
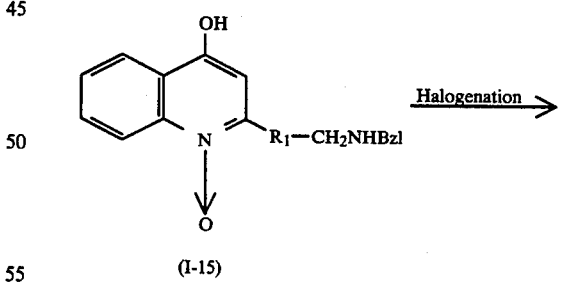
(I-15)
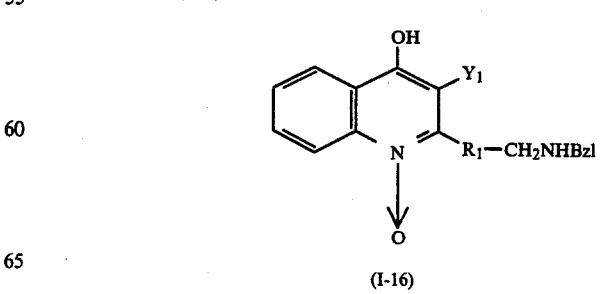
(I-16)

-continued

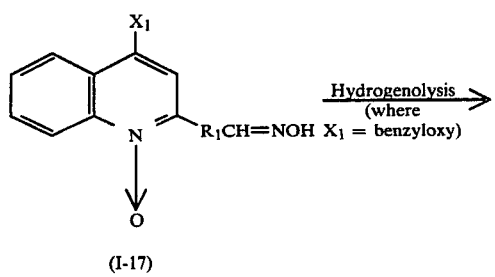

(I-17)

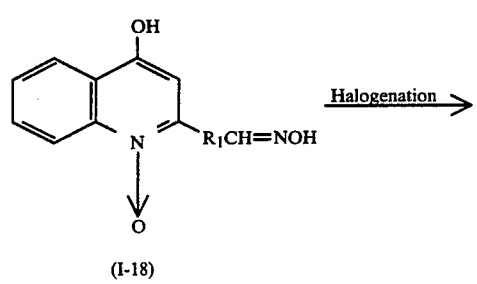

(I-18)

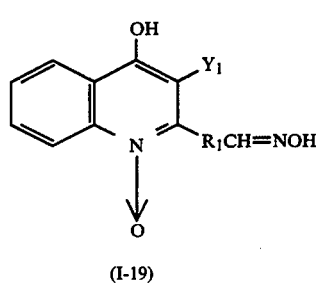

(I-19)

(I-7) —2,2-dimethoxypropane→

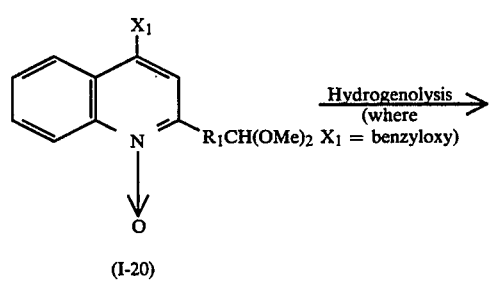

(I-20)

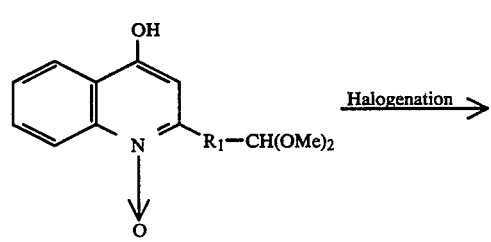

(I-21)

-continued

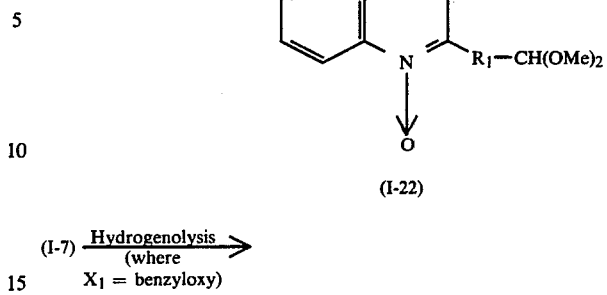

(I-22)

(I-7) —Hydrogenolysis→ (where $X_1$ = benzyloxy)

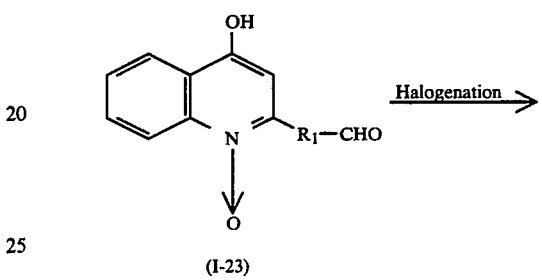

(I-23)

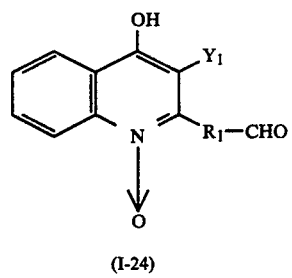

(I-24)

(wherein $X_1$ is X excluding hydroxy, that is, lower alkoxy, lower alkylthio, unsubstituted or substituted aralkyloxy, or unsubstituted or substituted aralkylthio; $Y_1$ is Y excluding hydrogen, that is, a halogen atom; $R_1$ has the same meaning as defined above; Hal is a halogen atom, for example, chlorine, bromine, and iodine).

First of all, compound (III) is prepared by reaction of compound (II) with a Grignard's reagent [prepared from $^tBu(Me)_2SiOCH_2R_1Hal$ and magnesium].

The reaction can be carried out in an ethereal solvent such as tetrahydrofuran, dioxane, etc. under mild conditions nearly at room temperature or below. It is preferable to use at least about one mole, preferably about 1.5 to about 2 moles of the Grignard's reagent per mole of the compound (II). After the reaction, the remaining excess Grignard's reagent is decomposed, for example, by adding water thereto, and then the solvent is removed therefrom by distillation. The residues thus obtained are dissolved in an appropriate inert solvent, for example, a halogenated hydrocarbon such as methylene chloride, chloroform, carbon tetrachloride, etc., and the solution is treated with an organic peroxide, for example, perbenzoic acid, m-chloroperbenzoic acid, peracetic acid, etc. in a substantially equimolar amount or a little excess amount, in respect to the compound (II), with ice cooling, whereby the compound (III) can be obtained.

The compound (III) thus obtained is subjected to hydrolysis reaction with hydrochloric acid, etc. in a solvent, for example, alcohol such as methanol, ethanol, propanol, etc., acetone, etc. at room temperature, whereby compound (I-1) can be obtained.

Then, the compound (I-1) is halogenated, if necessary, whereby compound (I-2) can be obtained. The halogenation can be carried out according to the ordinary procedure using the ordinary halogenating agent, such as N-chlorosuccinimide, N-bromosuccinimide, etc. For example, when the halogenation is carried out with N-halosuccinimide, the compound (I-1) is dissolved in an appropriate solvent, for example, an alcohol such as methanol, ethanol, etc., or a halogenated hydrocarbon such as dichloromethane, chloroform, etc., and a substantially equimolar amount of N-halosuccinimide is added thereto. Then, the mixture is stirred at room temperature, whereby the compound (I-1) can be converted to the compound (I-2).

On the other hand, the compound (I-1) is dissolved in an appropriate inert solvent, for example, a halogenated hydrocarbon such as methylene chloride, chloroform, carbon tetrachloride, etc., and treated with dihydropyran in a substantially equimolar amount or a little excess amount in respect to the compound (I-1) and a catalytic amount of p-toluenesulfonic acid or a catalytic amount of D-camphorsulfonic acid or the like at room temperature, whereby the compound (I-1) can be converted to compound (I-3). A compound (I-3) wherein $X_1$ is a benzyloxy group can be converted to compound (I-4) by a well-known hydrogenolysis reaction. For example, the compound (I-4) can be obtained by reducing the compound (I-3) with hydrogen under the atmospheric pressure or under a superatmospheric pressure at room temperature in a solvent such as methanol, ethanol, etc. in the presence of a hydrogenating catalyst such as palladium-carbon, platinum black, Raney nickel, etc. On the other hand, compound (I-5) can be obtained by hydrogenolyzing a compound (I-1) where $X_1$ is a benzyloxy group in the same manner as described above. Compound (I-6) can be obtained, if necessary, by halogenating the compound (I-5) in the same manner as described above. The compound (I-1) can be converted to compound (I-7) by dissolving the compound (I-1) in an appropriate inert solvent, for example, a halogenated hydrocarbon such as methylene chloride, chloroform, carbon tetrachloride, etc. and oxidizing the compound (I-1) with pyridinium chlorochromate in a substantially equimolar amount or an excess amount in respect to the compound (I-1) at room temperature.

Furthermore, the compound (I-7) can be converted to compound (I-8) by dissolving the compound (I-7) in a solvent such as acetone, etc., and treating the compound (I-7) with an excess amount of Jones' reagent with ice cooling. A compound (I-8) where $X_1$ is a benzyloxy group can be converted to compound (I-9) by hydrogenolysis in the same manner as above, and furthermore the compound (I-9) can be converted to compound (I-10), if necessary, by halogenation in the same manner as above.

On the other hand, the compound (I-7) can be converted to compound (I-11) by treating the compound (I-7) with ammonium acetate and sodium cyanoborohydride in a solvent such as methanol, ethanol, etc. with ice cooling. A compound (I-11) where $X_1$ is a benzyloxy group can be converted to compound (I-12) by hydrogenolysis in the same manner as above, and furthermore the compound (I-12) can be converted to compound (I-13), if necessary, by halogenation in the same manner as above.

The compound (I-7) can be converted to compound (I-14) by treatment with benzylamine in a solvent such as methanol, ethanol, etc. at room temperature and then by reduction with sodium borohydride with ice cooling. A compound (I-14) where $X_1$ is a benzyloxy group can be converted to compound (I-15) by hydrogenolysis in the same manner as above, and furthermore the compound (I-15) can be converted to compound (I-16), if necessary, by halogenation in the same manner as above.

Furthermore, the compound (I-7) can be converted to compound (I-17) by treatment with hydroxylamine hydrochloride at room temperature in a solvent such as methanol, ethanol, etc. A compound (I-17) where $X_1$ is a benzyloxy group can be converted to compound (I-18) by hydrogenolysis in the same manner as above, and furthermore the compound (I-18) can be converted to compound (I-19), if necessary, by halogenation in the same manner as above.

Furthermore, the compound (I-7) can be converted to compound (I-20) by adding compound (I-7) and 2,2-dimethoxypropane to an appropriate inert solvent such as methylene chloride, chloroform, carbon tetrachloride, etc. and stirring the mixture in the presence of an acid catalyst such as p-toluenesulfonic acid, D-camphorsulfonic acid, etc. at room temperature. A compound (I-20) where $X_1$ is a benzyloxy group can be converted to compound (I-21) by hydrogenolysis in the same manner as above, and the compound (I-21) can be converted to compound (I-22) by halogenation in the same manner as above.

Furthermore, a compound (I-7) where $X_1$ is a benzyloxy group can be converted to compound (I-23) by hydrogenolysis in the same manner as above, and the compound (I-23) can be converted to compound (I-24), if necessary, by halogenation in the same manner as above.

The compound (I) thus prepared, i.e. compounds (I-1) to (I-24) can be purified by a well-known purification procedure, for example, by recrystallization, column chromatography using silica gel, etc., extraction, etc.

The present invention also relates to a preventive and healing composition for diseases due to lipoxygenase metabolic products, which comprises an effective amount of a compound (I) or a pharmacologically acceptable salt thereof, and at least one pharmaceutically acceptable carrier. The compound (I) and its salts strongly inhibit the lipoxygenase activity. The compound (I) and its pharmacologically acceptable salts are useful for healing and preventing, or treating bronchial asthma, various allergic diseases (allergic rhimitis, urticaria, etc.), ischemic heart disease, hypertension, ischemic brain disturbance, arteriosclerosis, inflammatory diseases, etc., caused by lipoxygenase metabolites. Dosage for these purposes depends upon the desired healing effect, way of administration, healing period, age, body weight, etc., and usually is 0.5–20 mg/kg per day for an adult human as compounds (I) through oral or parenteral route (for example, injection, application, inhalation, etc.). Compound (I) or a salt thereof can be administered as such, but generally administered in the form of tablets, pills, powder, granules, capsules, suppository, injection, etc. Carriers used for the pharmaceutical composition include lactose, dextrose, sucrose, sorbitol, mannitol, glucose, cellulose, cyclodextrin, talc, starch, methylcellulose, gelatin, arabic gum, polyethylene glycol, carboxymethylcellulose, hydroxypropylcellulose, sodium benzoate, sodium hydrogen sulfite, aluminium stearate, magnesium stearate, mineral oil, vegetable oil, white vaseline, liquid paraffin, etc., and can be appropriately selected in view of the kind of preparations. The present composition can contain 0.01–85 weight percent of compound (I).

Examples and Experimental Example of the present invention are given below:

EXAMPLE 1

1-(1) Preparation of 4-benzyloxy-2-(11-t-butyldimethylsilyloxyundecyl) quinoline-N-oxide The Grignard's reagent prepared from 7.5 m moles of 11-t-butyldimethylsilyloxyundecyl bromide and 7.5 m moles of magnesium is dropwise added to a tetrahydrofuran solution containing 5 m moles of 4-benzyloxyquinoline-N-oxide with ice cooling and the mixture is stirred at the same temperature for one hour. Then, water is added by portions thereto to decompose the reagent, and then the mixture is extracted with chloroform. The solvent is removed from the extract by distillation, and the residue is dissolved in methylene chloride, and an aqueous saturated solution of sodium hydrogen carbonate is added to the solution, and further 5 m moles of ice-cooled metachloroperbenzoic acid is added thereto. Then, the mixture is stirred for 30 minutes. Then, the reaction solution is washed with an aqueous saturated solution of sodium hydrogen carbonate and then with water, and dried over anhydrous sodium sulfate. Then, the solvent is removed therefrom by distillation. The residue is purified by silica gel column procedure, whereby the captioned compound can be obtained as a colorless oily substance (yield: 88.0%).

NMR (CDCl$_3$) δ (ppm): 0.35(6H, s, Me×2), 0.86(9H, s, Me×3), 3.14(2H, t, J=6 Hz, ArCH$_2$), 3.61(2H, t, J=6 Hz, —OCH$_2$), 5.30(2H, s, OCH$_2$Ar), 6.70(1H, s, ArH), 8.28(1H, dd, J=1.5 Hz, 8 Hz, ArH), 8.87(1H, dd, J=1.5 Hz, 8 Hz, ArH)

1-(2) Preparation of 4-benzyloxy-2-(11-hydroxyundecyl) quinoline-N-oxide.

At first, 5 m moles of 4-benzyloxy-2-(11-t-butyldimethylsilyloxyundecyl) quinoline-N-oxide is dissolved in methanol, and an aqueous 10% hydrochloric acid solution is added thereto. Then, the mixture is stirred at room temperature for 3 hours. After removal of the solvent therefrom by distillation, the residue is extracted with chloroform, and the extract is washed with an aqueous saturated sodium hydrogen carbonate solution, and then with water, and dried over anhydrous sodium sulfate, and the solvent is removed therefrom by distillation. The residue is purified by silica gel column procedure, whereby the captioned compound is obtained as colorless crystals (yield: 88.4%).

NMR (CDCl$_3$) δ (ppm): 3.12(2H, t, J=7.5 Hz, ArCH$_2$), 3.60(2H, t, J=6 Hz, CH$_2$OH), 5.30(2H, s, OCH$_2$Ar), 6.69(1H, s, ArH), 8.25(1H, dd, J=1.5 Hz, 8 Hz, ArH), 8.79(1H, dd, J=1.5 Hz, 8.5 Hz, ArH).

EXAMPLE 2

In the same manner as in Example 1, 4-benzyloxy-2-(3-hydroxypropyl) quinoline-N-oxide is obtained.

NMR (CDCl$_3$+CD$_3$OD) δ (ppm): 2.40(2H, q, J=5 Hz, CH$_2$CH$_2$CH$_2$), 3.29(2H, t, J=5 Hz, Ar—CH$_2$—), 3.68 (2H, t, J=5 Hz, CH$_2$OH), 5.40(2H, s, —OCH$_2$Ar), 6.98(1H, s, ArH), 8.38(1H, dd, J=1.5 Hz, 8 Hz, ArH), 8.74(1H, dd, J=1.5 Hz, 8 Hz, ArH).

EXAMPLE 3

Preparation of 4-hydroxy-2-(11-hydroxyundecyl) quinoline-N-oxide

In this example, 4-benzyloxy-2-(11-hydroxyundecyl) quinoline-N-oxide is dissolved in methanol and catalytically reduced with a catalyst of 10% palladium-carbon under the atmospheric pressure. Then, the catalyst is removed therefrom by filtration, and the solvent is also removed therefrom by distillation. The residue is recrystallized from ethanol, whereby the cationed compound is obtained (yield: 57.5%).

NMR (CDCl$_3$+CD$_3$OD) δ (ppm): 2.91(2H, t, J=6 Hz, CH$_2$Ar), 3.57(2H, t, J=6 Hz, CH$_2$OH), 6.35(1H, s, ArH), 8.16(1H, dd, J=1.5 Hz, 8 Hz, ArH), 8.30(1H, dd, J=1.5 Hz, 8 Hz, ArH).

EXAMPLE 4

In the same manner as in Example 3, 4-hydroxy-2-[3-(2-tetrahydropyranyloxy) propyl] quinoline-N-oxide is obtained.

NMR (CDCl$_3$+CD$_3$OD) δ (ppm): 2.34(2H, q, J=6 Hz, —CH$_2$CH$_2$CH$_2$—), 2.90(2H, t, J=6 Hz, ArCH$_2$—), 4.54(1H, br.s,

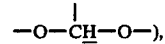

—O—CH—O—), 6.21(1H, s, ArH), 8.14(1H, dd, J=1.5 Hz, 8 Hz, ArH), 8.29(1H, dd, J=1.5 Hz, 8 Hz, ARH).

EXAMPLE 5

Preparation of 3-bromo-4-hydroxy-2-(11-hydroxyundecyl) quinoline-N-oxide

In this example, 1 m mole of 4-hydroxy-2-(11-hydroxyundecyl) quinoline-N-oxide is dissolved in a liquid mixture of methanol-chloroform (5:1), and 1 m mole of N-bromosuccinimide is added thereto. The mixture is stirred at room temperature for one hour. After the reaction, the solvent is removed therefrom by distillation, and the residue is recrystallized from ethanol, whereby the captioned compound is obtained (yield: 70.5%).

NMR (CDCl$_3$+CD$_3$OD) δ (ppm): 3.25(2H, t, J=6.5 Hz, ArCH$_2$—), 3.91(2H, t, J=6 Hz, CH$_2$OH), 7.96(1H, dd, J=1.5 Hz, 8 Hz, ArH), 8.36(1H, dd, J=1.5 Hz, 8 Hz, ArH).

EXAMPLE 6

Preparation of 4-benzyloxy-2-[11-(2-tetrahydropyranyloxy) undecyl] quinoline-N-oxide In this example, 5 m moles of 4-benzyloxy-2-(11-hydroxyundecyl)-quinoline-N-oxide is dissolved in dichloromethane, and a catalytic amount of D-camphorsulfonic acid and 6 m moles of 2,3-dihydropyran are added thereto. The mixture is stirred at room temperature for 3 hours. Then, the reaction solution is washed with an aqueous sodium hydrogen carbonate solution and then with water, and dried over anhydrous sodium sulfate. The solvent is removed therefrom by distillation, and the residue is purified by silica gel column procedure, whereby the cationed compound is obtained as a colorless oily substance (yield: 82.3%).

NMR (CDCL$_3$) δ (ppm): 3.13(2H, t, J=6.5 Hz, CH$_2$Ar), 4.55(1H, t, J=2 Hz,

5.27(2H, s, OC$\underline{H}_2$Ar), 6.68(1H, s, Ar$\underline{H}$), 8.27(1H, dd, J=1.5 Hz, 8 Hz, Ar$\underline{H}$), 8.83(1H, dd, J=1.5 Hz, 8 Hz, Ar$\underline{H}$).

EXAMPLE 7

Preparation of 4-benzyloxy-2-(10-formyldecyl) quinoline-N-oxide

In this example, 5 m moles of 4-benzyloxy-2-(11-hydroxyundecyl) quinoline-N-oxide is dissolved in dichloromethane, and 15 m moles of pyridinium chlorochromate is added thereto. Then, the mixture is stirred at room temperature for 2.5 hours. The reaction solution is washed with water and dried over anhydrous sodium sulfate, and the solvent is removed therefrom by distillation. The residue is purified by silica gel column procedure, whereby the captioned compound is obtained as a colorless oily substance (yield: 79.2%).

NMR (CDCl$_3$) δ (ppm): 2.40(2H, t, J=6 Hz, C$\underline{H}_2$Ar), 3.16(2H, t, J=8 Hz, C$\underline{H}_2$CHO), 5.31(2H, s, OC$\underline{H}_2$Ar), 6.70(1H, s, Ar$\underline{H}$), 8.26(1H, dd, J=1.5 Hz, 8 Hz, Ar$\underline{H}$), 8.84(1H, dd, J=1.5 Hz, 8 Hz, Ar$\underline{H}$), 9.77(1H, 6, J=2 Hz, C$\underline{H}$O).

EXAMPLE 8

Preparation of 4-benzyloxy-2-(10-carboxydecyl) quinoline-N-oxide

In this example, 5 m moles of 4-benzyloxy-2-(10-formyldecyl) quinoline-N-oxide is dissolved in acetone, and 10 m moles of Jones' reagent prepared from chromium trioxide, sulfuric acid and water is added thereto with ice cooling. The mixture is stirred for 5 minutes. After the reaction, water is added thereto, and the reaction mixture is extracted with chloroform. The extract is dried over anhydrous sodium sulfate, and then the solvent is removed therefrom by distillation. The residue is purified by silica gel column procedure, whereby the captioned compound is obtained as colorless crystals (yield: 31.0%).

NMR (CDCl$_3$) δ (ppm): 2.32(2H, t, J=6.5 Hz, C$\underline{H}_2$Ar), 3.22(2H, t, J=8.0 Hz, C$\underline{H}_2$CO$_2$H), 5.33(2H, s, OC$\underline{H}_2$Ar), 6.76(1H, s, Ar$\underline{H}$), 8.32(1H, dd, J=1 Hz, 8 Hz, Ar$\underline{H}$), 8.83(1H, dd, J=1 Hz, 8 Hz, Ar$\underline{H}$).

EXAMPLE 9

Preparation of 4-benzyloxy-2-(11-aminoundecyl) quinoline-N-oxide

In this example, 5 m moles of 4-benzyloxy-2-(10-formyldecyl) quinoline-N-oxide is dissolved in methanol, and 50 m moles of ammonium acetate and 15 m moles of sodium cyanoborohydride are added thereto with ice cooling. Then, the mixture is stirred for 1.5 hours. After the reaction, the solvent is removed therefrom by distillation, and then the mixture is extracted with chloroform. The chloroform layer is dried over anhydrous sodium sulfate, and the solvent is removed therefrom by distillation. The residue is purified by silica gel column procedure, whereby the captioned compound is obtained as colorless crystals (yield: 21.5%).

NMR (CDCl$_3$) δ (ppm): 2.60(2H, br.s, C$\underline{H}_2$NH$_2$), 3.16 (2H, t, J=8 Hz, C$\underline{H}_2$Ar), 5.30(2H, s, OC$\underline{H}_2$Ar), 6.71(1H, s, Ar$\underline{H}$), 8.30(1H, dd, J=1 Hz, 8 Hz, Ar$\underline{H}$), 8.85(1H, dd, J=1 Hz, 8 Hz, Ar$\underline{H}$).

EXAMPLE 10

Preparation of 4-benzyloxy-2-[11-(N-benzylaminoundecyl)] quinoline-N-oxide

In this example, 5 m moles of 4-benzyloxy-2-(10-formyldecyl) quinoline-N-oxide is dissolved in ethanol, and 5 m moles of benzylamine is added thereto. Then, the mixture is stirred at room temperature for two hours. Then, the solvent is removed therefrom by distillation, and an aqueous saturated sodium hydrogen carbonate solution is added to the residue. Then, the mixture is extracted with chloroform. The solvent is removed therefrom by distillation, and the residue is dissolved in methanol, and 10 m moles of sodium borohydride is added thereto. The mixture is stirred with ice cooling for one hour. The solvent is removed therefrom by distillation, and the residue is extracted with chloroform. The chloroform layer is dried over anhydrous sodium sulfate, and then the solvent is removed therefrom by distillation. The residue is purified by silica gel column procedure, whereby the captioned compound is obtained as a colorless oily substance (yield: 65.5%).

NMR (CDCl$_3$) δ (ppm): 2.62(2H, t, J=6.5 Hz, NHC$\underline{H}_2$), 3.15(2H, t, J=8 Hz, C$\underline{H}_2$Ar), 3.89(2H, s, NHC$\underline{H}_2$Ar), 5.30(2H, s, OC$\underline{H}_2$Ar), 6.68(1H, s, Ar$\underline{H}$), 8.26 (1H, dd, J=1 Hz, 8 Hz, Ar$\underline{H}$), 8.86(1H, dd, J=1 Hz, 8 Hz, Ar$\underline{H}$).

EXAMPLE 11

Preparation of 4-benzyloxy-2-[10-(N-hydroxyiminodecyl)] quinoline-N-oxide

In this example, 5 m moles of 4-benzyloxy-2-(10-formyldecyl) quinoline-N-oxide is dissolved in methanol and 5 m moles of hydroxylamine hydrochloride is added thereto. The mixture is stirred at room temperature for 3 hours. The solvent is removed therefrom by distillation, and an aqueous saturated sodium hydrogen carbonate solution is added to the residue. Then, the mixture is extracted with chlorofrm, and the organic layer is dried over anhydrous sodium sulfate. Then, the solvent is removed therefrom by distillation, and the residue is purified by silica gel column procedure, whereby the captioned compound is obtained as a colorless oily substance (yield: 72.0%).

NMR (CDCl$_3$) δ (ppm): 2.15(1H, q, J=6 Hz, HC$\underline{H}$—CH=N—), 2.30(1H, q, J=6 Hz, HC$\underline{H}$—CH=N—), 3.17(2H, t, J=8 Hz, C$\underline{H}_2$Ar), 5.31(2H, s, OC$\underline{H}_2$Ar), 6.71(1H, s, Ar$\underline{H}$), 8.28(1H, dd, J=1 Hz, 8 Hz, Ar$\underline{H}$), 8.89(1H, dd, J=1 Hz, 8 Hz, Ar$\underline{H}$).

EXAMPLE 12

Preparation of 4-benzyloxy-2-(11,11-dimethoxyundecyl) quinoline-N-oxide

In this example, 5 m moles of 4-benzyloxy-2-(10-formyldecyl) quinoline-N-oxide is dissolved in dichloromethane, and a catalytic amount of D-camphorsulfonic acid and a large excess of 2,2-dimethoxypropane are added thereto. The mixture is stirred at room temperature for 3 hours. After the reaction, the reaction solution is washed with an aqueous saturated sodium hydrogen carbonate solution, and then with water, and dried over anhydrous sodium sulfate. After removal of the solvent by distillation, the residue is purified by silica gel column procedure, whereby the captioned compound is obtained as a colorless oily substance (yield: 70.6%).

NMR (CDCl$_3$) δ (ppm): 3.16(2H, t, J=7 Hz, C$\underline{H}_2$Ar), 3.36(6H, s, OMe×2), 4.38(1H, t, J=5 Hz, C$\underline{H}$(OMe)$_2$), 5.32(2H, s, OCH$_2$Ar), 6.71(1H, s, ArH), 8.30 (1H, dd, J=1 Hz, 8 Hz, ArH), 8.87(1H, dd, J=1 Hz, 8 Hz, ArH).

EXAMPLES 13-20

In the same manner as in Examples 1 and 3, compounds shown in the following Table 1 are obtained.

TABLE 1

| Ex. No. | Compound | NMR δ(ppm) |
|---|---|---|
| 13 | 4-benzyloxy-2-[3-(2-tetrahydropyranyloxy) propyl] quinoline-N—oxide | CDCl$_3$, 2.12(2H, t, J=7.5Hz, CH$_2$CH$_2$CH$_2$), 3.23(2H, t, J=8Hz, CH$_2$Ar), 4.54(1H, br.s, —OCHO—), 5.26(2H, s, OCH$_2$Ar), 6.76(1H, s, ArH), 8.22(1H, dd, J=1.5Hz, 8Hz, ArH), 8.76(1H, d, J=8Hz, ArH) |
| 14 | 4-hydroxy-2-[11-(2-tetrahydropyranyloxy) undecyl] quinoline-N—oxide | CDCl$_3$, 2.43(2H, t, J=7Hz, CH$_2$Ar), 4.58(1H, br.s, —OCHO—), 5.99(1H, s, ArH), 7.17–8.32 (4H, m, ArH) |
| 15 | 4-hydroxy-2-(10-carboxydecyl) quinoline-N—oxide | CDCl$_3$ + CD$_3$OD, 2.30(2H, t, J=7.5Hz, CH$_2$CO$_2$H), 2.95(2H, t, J=8Hz, CH$_2$Ar), 6.36(1H, s, ArH), 7.4–8.40(4H, m, ArH) |
| 16 | 4-hydroxy-2-(11-aminoundecyl) quinoline-N—oxide. hydrochloride | CDCl$_3$ + CD$_3$OD, 2.99(2H, t, J=7.5Hz, CH$_2$NH$_2$), 3.25(2H, t, J=8Hz, CH$_2$Ar), 7.16(1H, s, ArH), 7.77–8.60(4H, m, ArH) |
| 17 | 4-hydroxy-2-[11-(N—benzylaminoundecyl)] quinoline-N—oxide | CDCl$_3$, 2.50(2H, br.s, CH$_2$NHCH$_2$—Ar), 2.72(2H, dist.t, J=7.5Hz, ArCH$_2$), 3.93(2H, s, CH$_2$NHAr), 5.88(1H, s, ArH), 7.99(1H, d, J=8Hz, ArH), 8.17(1H, d, J=8Hz, ArH) |
| 18 | 4-hydroxy-2-[10-(N—hydroxyiminodecyl)] quinoline-N—oxide | CDCl$_3$, 2.16(2H, q, J=5Hz, CH$_2$CH=N—), 2.99(2H, t, J=6Hz, CH$_2$Ar), 6.46(1H, s, ArH), 6.68(1H, t, J=5Hz, CH=N—), 7.35–8.40(4H, m, ArH) |
| 19 | 4-hydroxy-2-(11,11-dimethoxyundecyl) quinoline-N—oxide | CDCl$_3$, 2.48(2H, t, J=8Hz, CH$_2$Ar), 3.36(6H, s, OMe x 2), 4.42(1H, t, J=6Hz, CH(OMe)$_2$), 6.04(1H, s, ArH), 7.30–8.35 (4H, m, ArH) |
| 20 | 4-hydroxy-2-(10-formyldecyl) quinoline-N—oxide | CDCl$_3$, 2.40(2H, t, J=8Hz, ArCH$_2$), 2.81(2H, br.s, CH$_2$CHO), 6.40(1H, s, ArH), 8.10(1H, d, J=8Hz, ArH), 8.30(1H, d, J=8Hz, ArH), 9.77(1H, t, J=2Hz, CHO) |

EXAMPLE 21

Tablets

A 10% hydroxypropylcellulose solution is added to a mixture consisting of 100 g of 4-benzyloxy-2-(11-hydroxyundecyl) quinoline-N-oxide, 40 g of lactose, 18 g of corn starch and 10 g of carboxymethylcellulose calcium, and the mixture is kneaded. The mixture is then granulated by an extrusion granulator with 1.0 mm basket, and the granules are dried at 60° C. The dried granules are screened on a 16-mesh sieve, and magnesium stearate is added to the screened granules to prepare tabletting granules. According to the ordinary procedure, tablets, 8 mm in size, each containing 100 mg of the N-oxide in one tablet (170 mg), are prepared.

EXAMPLE 22

Capsules

A 10% hydroxypropylcellulose solution is added to a mixture consisting of 50 g of 4-benzyloxy-2-(10-carboxydecyl) quinoline-N-oxide, 80 g of lactose and 38 g of potato starch, and the mixture is kneaded. The mixture is granulated in the same manner as in Example 21, and after addition of magnesium stearate, capsules each containing 50 mg of the N-oxide in one capsule (170 mg) are prepared according to an ordinary procedure.

EXAMPLE 23

Soft Capsules

At first, 10 g of 4-hydroxy-2-[11-(2-tetrahydropyranyloxy) undecyl] quinoline-N-oxide is dissolved in 100 g of soybean oil, and the solution is filled into capsules, each containing 10 mg of the N-oxide, according to the ordinary procedure, to prepare soft capsules.

EXAMPLE 24

Ointment

At first, 20 g of 4-hydroxy-2-(11,11-dimethoxyundecyl) quinoline-N-oxide is mixed with a mixture of white vaseline and liquid paraffin to prepare an ointment containing 100 mg/g of the N-oxide.

Experimental Example

Inhibiting actions of test compounds shown in Table 2 on lipoxygenase in vitro were determined according to the following procedure.

Procedure for determining inhibiting actions on leukocyte 5-lipoxygenase:

Determination was conducted according to the modified B. A. Jakschik et al procedure [Biochim. Biophys. Res. Commun. 95, 103 (1980)]. That is, Leukemic basophilic granulocyte (RBL-1, ATCC NO. CRL 1378) cells of rats were used as a 5-lipoxygenase enzyme source, and the cells and a test compound were contacted with each other in a 0.07 M tris hydrochloric acid buffer solution in the presence of 0.7 μm moles of calcium chloride at 37° C. for 5 minutes, and then 20 μmoles of [$^{14}$C]-arachidonic acid was added thereto. The mixture was subjected to reaction at 37° C. for 5 minutes. The reaction product was extracted with ethyl acetate/methanol/0.2 M citric acid (30/4/1) and the extract was subjected to a thin layer chromatographic separation (developing solvent: petroleum ether/ethyl ether/acetic acid=50/50/1), and the spot of 5-hydroxy-5,8,10,14-eicosatetraenoic acid in the product was scraped off and $^{14}$C was measured by a liquid scintillation counter.

The result is shown in Table 2, from which it is obvious that the test compounds show an inhibiting action on the 5-lipoxygenase enzyme. The well-known compound BW-755C, i.e. 3-amino-1-(3-trifluoromethylphenyl)-2-pyrazoline hydrochloride is shown for comparison in Table 2.

TABLE 2

| Compound Ex. No. | 5-lipoxygenase-inhibiting activity IC$_{50}$ (μM), or %*2 | Compound Ex. No. | 5-lipoxygenase-inhibiting activity IC$_{50}$ (μM), or %*1 |
|---|---|---|---|
| 2 | 2.7% *2 | 4 | 1.6% *2 |
| 13 | 11.5% *2 | 3 | 0.28 *1 |
| 1-(2) | 7.7% *2 | 14 | 0.16 *1 |
| 6 | 20.0% *2 | 20 | 1.7 *1 |
| 7 | 33.1% *2 | 15 | 2.7 *1 |
| 8 | 27.3% *2 | 16 | 0.25 *1 |
| 9 | 27.0% *2 | 17 | 0.27 *1 |
| 10 | 32.4% *2 | 18 | 0.46 *1 |
| 11 | 36.6% *2 | 19 | 0.18 *1 |
| 12 | 37.2% *2 | 5 | 0.22 *1 |

TABLE 2-continued

| Compound Ex. No. | 5-lipoxygenase-inhibiting activity IC$_{50}$ ($\mu$M), or %*2 | Compound Ex. No. | 5-lipoxygenase-inhibiting activity IC$_{50}$ ($\mu$M), or %*1 |
| --- | --- | --- | --- |
|  |  | BW-755C | 4.0 |

*1 Concentration of compound required for 50% inhibition of the enzyme activity.
*2 Percent inhibition at 1 $\mu$M compound concentration

What is claimed is:

1. A quinoline-N-oxide derivative represented by the formula:

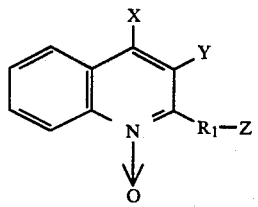

wherein X is hydroxy; lower alkoxy, lower alkylthio, unsubstituted or substituted aralkyloxy, or unsubstiacuted or substituted aralkylthio; Y is a hydrogen atom or halogen atom;

R$_1$ is alkylene or alkenylene having 3 to 15 carbon atoms; Z is hydroxymethyl, lower alkoxymethyl, unsubstituted or substituted aryloxymethyl, tetrahydropyranyloxymethyl, tetrahydrofuranyloxymethyl, lower alkylthiomethyl, unsubstituted or substituted arylthiomethyl, aminomethyl,

—CH$_2$NHR$_2$ wherein R$_2$ is lower alkyl, unsubstituted or substituted aralkyl, or unsubstituted or substituted aryl,

—CH2NR3R4 wherein R$_3$ and R$_4$ are lower alkyl, unsubtituted or substituted aralkyl, or unsubstituted or substituted aryl,

—CH$_2$N$^+$R$_5$R$_6$R$_7$ wherein R$_5$, R$_6$ and R$_7$ are lower alkyl, unsubstituted or substituted aralkyl, or unsubstituted or substituted aryl, where the counterion is a pharmacologically acceptable anion of an acid or a hydroxyl ion,

COR$_8$ wherein R$_8$ is a hydrogen atom, lower alkyl or hydroxy

—CH(OR$_9$)$_2$ wherein R$_9$ is lower alkyl, iminomethyl, hydroxyiminomethyl, or a halogen atom, provided that the substituent in the substituted aralkyloxy, the substituted aralkylthio, the substituted aralkyl, the substituted aryloxymethyl, the substituted arylthiomethyl, and the substituent aryl is a substituent on the aryl ring and is selected from the group consisting of lower alkyl, lower alkoxy, halogen atom, nitro and hydroxy, and pharmacologically acceptable salts thereof.

2. A quinoline-N-oxide derivative and its salts according to claim 1, wherein R$_1$ is alkylene or alkenylene having 5 to 15 carbon atoms.

3. A quinoline-N-oxide derivative and its according to claim 1, wherein said salts and pharmacologically acceptable base addition salts or pharmacologically acceptable acid addition salts.

4. A preventive and healing composition for diseases due to lipoxygenase metabolic products, which comprises an effective amount of a compound defined by claim 1, and at least one pharmaceutically acceptable carrier.

* * * * *